United States Patent [19]

Blanchard

[11] 4,062,728

[45] Dec. 13, 1977

[54] STARCH THINNING PROCESS

[75] Inventor: Paul H. Blanchard, Concord, Calif.

[73] Assignee: Amstar Corporation, New York, N.Y.

[21] Appl. No.: 595,010

[22] Filed: July 11, 1975

[51] Int. Cl.$^2$ ............................................. C12D 13/02
[52] U.S. Cl. .................................................. 195/31 R
[58] Field of Search ........................ 195/31 R, 11, 7; 127/29

[56] References Cited

U.S. PATENT DOCUMENTS

| | | | |
|---|---|---|---|
| 3,371,018 | 2/1968 | Ewing et al. | 195/31 R |
| 3,551,293 | 12/1970 | Seidman et al. | 195/31 R |
| 3,654,081 | 4/1972 | Vance et al. | 195/31 R |
| 3,804,715 | 4/1974 | Sugimoto et al. | 195/31 R |
| 3,849,194 | 11/1974 | Armbruster et al. | 195/31 R |
| 3,853,706 | 12/1974 | Armbruster et al. | 195/31 R |
| 3,912,590 | 10/1975 | Slott et al. | 195/31 R |

OTHER PUBLICATIONS

Madsen et al., "A New Heat Stable Bacterial Amylase and its Use in High Temperature Liquification," *Die Starke*, vol. 25, No. 9, pp. 306–308 (1973).

Primary Examiner—Raymond N. Jones
Assistant Examiner—Thomas G. Wiseman
Attorney, Agent, or Firm—Cooper, Dunham, Clark, Griffin & Moran

[57] ABSTRACT

A starch thinning process employing α-amylase is carried out in two stages. In the first stage, a high temperature and high pressure operation, the aqueous starch suspension to be thinned is maintained therein for about 8 minutes at a temperature of about 100° C. and then held at a temperature of about 150° C. for about 5 minutes. Thereupon, the resulting treated aqueous starch suspension from the first stage is cooled and introduced into the second stage operation wherein it is maintained in contact with additionally added α-amylase for a period of time of about 90 minutes at atmospheric pressure at a temperature of about 96° C. The resulting aqueous thinned starch product has a D.E. value in the range about 10–15.

15 Claims, 1 Drawing Figure

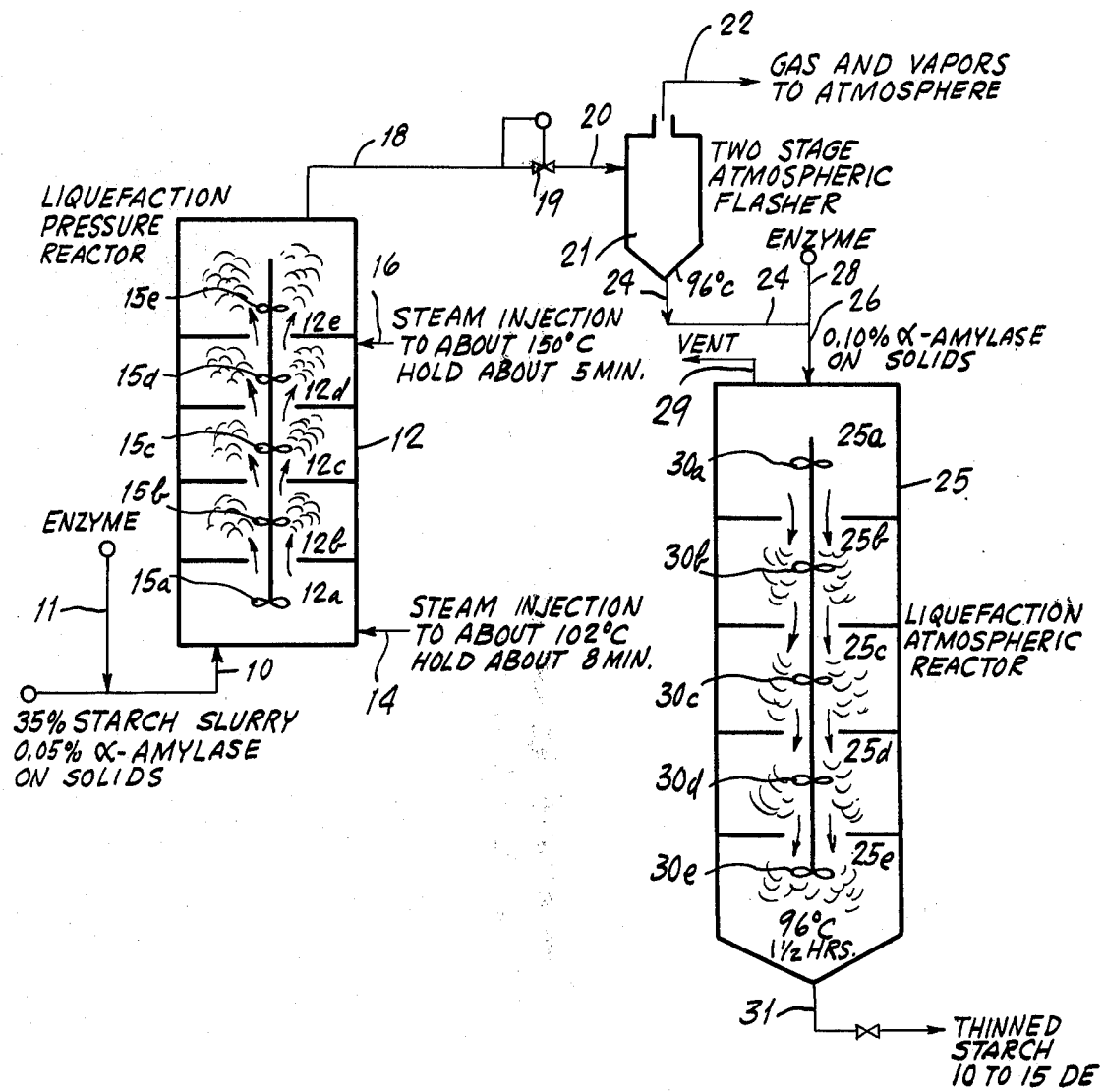

STARCH THINNING PROCESS

This invention relates to the thinning of starch. More particularly, this invention relates to the enzymatic thinning of an aqueous starch suspension. Still more particularly, this invention relates to the enzymatic thinning of an aqueous starch suspension employing α-amylase as the enzyme.

It is known to employ α-amylase as the emzyme in an enzymatic process for the thinning of starch. It is also known to produce thinned aqueous starch suspensions employing α-amylase in the starch thinning or hydrolyzing operation and then to enzymatically convert the resulting thinned starch to dextrose via another enzyme, viz. amyloglucosidase, to produce a solution containing substantially only dextrose dissolved therein. The above-indicated combination of enzymatic processes employing in sequence α-amylase and amyloglucosidase to effect saccharification of the α-amylase thinned starch to produce dextrose are conventional commercial processes. It is also known to convert enzymatically saccharified starch solution containing essentially dextrose to an aqueous solution containing substantially equimolar mixtures of dextrose and levulose by means of the enzyme glucose isomerase.

From the above it can be appreciated that the initial enzymatic thinning or hydrolyzation of starch via the enzyme α-amylase is an important operation since it is the first step in the enzymatic process employed for the conversion of starch, such as corn starch, to dextrose, or eventually, if desired, to dextrose and levulose.

Various techniques and processes are known for the enzymatic thinning or hydrolyzing of aqueous starch suspensions, particularly aqueous suspensions of corn starch, see particularly U.S. Pat. Nos. 2,280,006, 3,285,776 as well as U.S. Pat. No. 3,849,194 and 3,551,293, 3,371,018 and 3,853,706. The disclosures of these patents are herein incorporated and made part of this disclosure. For the most part, however, processes and techniques known heretofore for the thinning or hydrolyzing of aqueous starch suspensions employing α-amylase have not been completely satisfactory.

It is an object of this invention to provide an improved process for the enzymatic thinning or hydrolyzing of aqueous starch suspensions employing the enzyme α-amylase.

Another object of this invention is to provide a continuous process for thinning or partially hydrolyzing aqueous starch suspensions employing the enzyme α-amylase.

Still another object of this invention is to provide a process capable of high productivity employing α-amylase for the thinning of aqueous starch suspensions, particularly aqueous corn starch suspensions.

In at least one embodiment of the practice of this invention at least one of the foregoing objects will be achieved.

How these and other objects of this invention are accomplished will become apparent in the light of the accompanying disclosure made with reference to the accompanying drawing which schematically illustrates a flow scheme embodying a practice of this invention and particularly directed to the thinning of aqueous corn starch suspensions employing the enzyme α-amylase.

In accordance with this invention it has been discovered that an improved process for the enzymatic thinning or hydrolyzing of starch in aqueous starch suspensions and employing α-amylase is provided by carrying out the thinning or hydrolyzation of starch in the aqueous starch suspension in the presence of the enzyme α-amylase in two stages, the first stage being carried out at an elevated temperature and at a superatmospheric pressure sufficient to maintain the aqueous starch suspension undergoing treatment in the liquid phase. The second stage of the two stage starch thinning or hydrolyzing operation receives the resulting treated starch suspension from the first stage and, desirably upon the addition of additional α-amylase, the aqueous starch suspension is then subjected to further treatment at atmospheric pressure and at a temperature of about 100° C. or less, e.g. 93° C., for a sufficient period of time to produce the desired aqueous thinned starch product, such as an aqueous thinned starch product having a D.E. value in the range 10–20.

In the first stage operation in accordance with this invention the superatmospheric pressure employed is sufficient to maintain the aqueous starch suspension undergoing treatment therein in the liquid phase, i.e. sufficient pressure is employed in the first stage operation to prevent the formation of two phases, a liquid phase and a gaseous phase made up of steam vaporized from the aqueous starch suspension undergoing treatment. Specifically, sufficient pressure is employed in the first stage operation such that the pressure employed exceeds the vapor pressure of the aqueous starch suspension undergoing treatment. The pressure employed in the first stage operation is dependent upon the temperature employed in the first stage operation, usually a pressure of at least about 60 psig, such as in the range 60–200 psig, more or less, is adequate, particularly when the temperature employed in the first stage operation is in the range from about, slightly above 100° C., e.g. 102° C., up to about 150°–170° C., more or less.

The residence time of the aqueous starch suspension undergoing treatment in the first stage operation varies to some extent upon the temperatures employed in the first stage operation. Usually, a total residence time in the first stage operation in the range from about 5–10 minutes to about 15–30 minutes, more or less, is sufficient.

In the operation of the first stage thinning operation in accordance with this invention two temperature levels are employed. When the aqueous starch suspension to be thinned is initially introduced to the first stage thinning operation the aqueous starch suspension is maintained therein at a temperature from about 100° C. or slightly above, e.g. 102° C. to about 105°–110° C. for a suitable period of time, at least about 3–5 minutes, such as about 5–15 minutes, e.g. 8 minutes. Thereupon, after this initial treatment in the first stage operation the temperature of the aqueous starch suspension undergoing treatment in the first stage is increased to an elevated final temperature of at least about 135°–145° C., e.g. 140° C., or preferably higher, such as a temperature in the range about 150°–170° C., more or less, and maintained at this elevated final temperature within the first stage for a relatively short period of time, such as for at least about 3 minutes, such as about 5–15 minutes, usually about 5–10 minutes, more or less. Thereupon, the resulting treated aqueous starch suspension leaves the superatmospheric, high temperature first stage operation for further treatment in the second stage operation. In the high pressure and relatively high temperature first stage operation it is usually convenient to employ an aqueous starch suspension containing about 35% by weight starch, such as an aqueous starch suspension having a starch content in the range from about 25 to about 40% by weight. There is incorporated in the aqueous starch suspension, preferably just before it is introduced into the first stage operation a minor or small amount of α-amylase, such as an amount of α-amylase in the range about 0.03-0.10% by weight based on the starch content of the aqueous starch suspension, usually an amount of about 0.05% by weight α-amylase. The temperature of the aqueous starch suspension introduced into the first stage operation, both during the initial and final treatments therein, is usefully maintained by direct steam injection into the aqueous starch suspension.

In the preparation of the aqueous starch suspension for introduction into the first stage, it is desirable to employ in the make-up of the aqueous starch suspension softened water, i.e. water with a low dissolved solids content. Desirably, the suspension is adjusted to about a neutral pH, such as a pH in the range 6-7, e.g. 6.5, by the addition thereto of sodium carbonate. Also, in order to increase the efficacy of the α-amylase a minimum calcium ion or dissolved calcium concentration is maintained in the aqueous starch suspension, such as a dissolved calcium concentration of at least 10 ppm, such as in the range at least 5-10 ppm. Usually, this desirable dissolved calcium or calcium ion concentration is readily obtainable in untreated water or water treated with sodium carbonate for softening.

Upon completion of the first stage high pressure, high temperature treatment operation in accordance with this invention, the resulting treated aqueous starch suspension enters the second stage treatment operation wherein the aqueous starch suspension is subjected to further treatment in the presence of α-amylase at atmospheric pressure and at a temperature below 100° C., such as a temperature in the range 90°-98° C., such as a temperature in the range 93°-96° C.

Upon leaving the first stage operation and before being subjected to the second stage treatment operation the aqueous starch suspension undergoing treatment must be cooled. Cooling of the aqueous starch suspension leaving the first stage operation before introduction into the second stage operation can be effected by indirect heat exchange with a suitable coolant, such as water. It is convenient in accordance with one embodiment of the practice of this invention to cool the high temperature, high pressure aqueous starch suspension leaving the first stage operation by pressure reduction evaporative cooling or flashing the aqueous starch suspension to a relatively reduced or atmospheric pressure whereby the high temperature, high pressure aqueous starch suspension upon sudden reduction in pressure undergoes evaporative cooling.

The resulting cooled first stage treated aqueous starch suspension is then subjected to the second stage operation carried out at ambient or atmospheric pressure and at a temperature in the range about 100°-90° C. and desirably in the presence of added α-amylase, such as added α-amylase in the amount 0.1-0.2% by weight based on the original starch content in the aqueous starch suspension operation, usually an amount of α-amylase of about 0.15%.

In the second stage operation carried out at atmospheric pressure and at a temperature of about 93°-100° C. the aqueous starch suspension undergoing treatment is maintained at the above-indicated temperature in the presence of α-amylase for a period of time in the range from about 60 minutes to about 120-150 minutes, more or less. After the above-indicated residence time of the aqueous starch suspension in the second stage operation the resulting thinned aqueous starch suspension is withdrawn as product, such as an aqueous thinned starch product having a D.E. value in the range 10-20, such as a D.E. value of about 12-15, more or less. If desired, for purposes of temperature control during the second stage operation, the second stage reactor or reaction zone wherein the second stage thinning operation is being carried out may be jacketed and provided with a suitable heating and/or cooling fluid to maintain the desired temperature within the second stage treating operation, either isothermal operation or a temperature gradient therein from one end of the second stage reactor where the thinned aqueous starch suspension is introduced for treatment to the other end where the resulting thinned aqueous starch suspension is withdrawn as the thinned starch product having the desired D.E. value.

Reference is now made to the accompanying drawing which schematically illustrates a flow scheme illustrative of one embodiment of the practice of this invention involving the treatment of a 35% by weight aqueous starch slurry for the production therefrom of an aqueous thinned starch product having a D.E. value in the range 10-15. As shown in the drawing, a 35% slurry from a suitable source, not shown, is supplied via line 10 in admixture with about 0.05% by weight α-amylase based on the solids (starch) content of the aqueous starch slurry supplied from a suitable source, not shown, via line 11 is introduced into the bottom portion of first stage reactor 12. Steam via line 14 is introduced into the bottom portion of reactor 12 via line 14 for admixture with the aqueous starch suspension therein so as to bring the aqueous starch suspension in the lower portion of first stage reactor 12 to a temperature in the range 99°-110° C., such as a temperature of about 102° C.

As illustrated in the drawing, first stage reactor 12 is a vertically disposed reactor provided with open compartments 12a, 12b, 12c, 12d and 12e, each of said compartments desirably being provided with mixing or agitating means 15a, 15b, 15c, 15d, 15e, respectively. As illustrated, the aqueous starch suspension introduced into reactor 12 for treatment therein moves upwardly in serial flow from one compartment to the next upper compartment, provision being made within the reactor to eliminate or reduce to a minimum any backflow or back-mixing of the aqueous starch suspension from an upper compartment to the next lower compartment. By controlling the rate of introduction of the aqueous starch suspension introduced into the bottom or lower portion of reactor 12 the residence time of the aqueous starch suspension in the lower portion of reactor 12 is maintained therein at a temperature in the range about 100°-110° C. for the desired period of time, e.g. about 8 minutes.

As shown in the drawing, the aqueous starch suspension undergoing treatment in first stage reactor 12 moves upwardly therein and at about the last stage steam is introduced into the upper portion of reactor 12 via line 16 so as to bring the aqueous starch suspension in the upper portion of reactor 12 to an elevated temperature of about 145°-155° C., such as 150°C.

In the operation of first stage reactor 12 which is maintained liquid full sufficient pressure is maintained therein, such as a pressure of at least 60 psig, to maintain the aqueous starch suspension introduced thereinto via line 10 in single phase, i.e. the applied pressure is sufficient to prevent any boiling of the aqueous starch suspension therein and two-phase flow within reactor 12 does not occur.

In first stage reactor 12 the aqueous starch suspension is maintained at an elevated temperature of about 150° C. in the upper portion thereof for a suitable period of time of about 5 to 8 minutes, more or less. Although reactor 12 is illustrated as comprising five stages, this illustration is for convenience only since reactor 12 might comprise substantially more compartments, as many as 15 or more.

Upon completion of the thinning operation within first stage reactor 12 the resulting partially thinned aqueous starch suspension at an elevated pressure of about 60 psig is removed from the top thereof via line 18 and then moves through pressure reducing valve 19 from which the resulting aqueous starch suspension is supplied via line 20 into evaporative flasher 21, such as a two-stage atmospheric cyclone-type flasher. Gases, such as air, and vapors are removed from atmospheric flasher 21 for disposal via line 22 and the resulting flashed, cooled liquid aqueous starch suspension is recovered from flasher 21 at substantially atmospheric pressure and at a temperature of about 96° C. via line 24 and supplied to the upper portion of second stage atmospheric reactor 25 via line 26 in admixture with added α-amylase supplied from a suitable source, not shown, via line 28. The amount of α-amylase added to the partially thinned aqueous starch slurry supplied to second stage atmospheric reactor 25 via line 26 is in the range about 0.1–0.2% by weight based on the starch originally supplied to first stage reactor 12 via line 10, such as an amount of about 0.15% by weight α-amylase.

As illustrated, second stage atmospheric reactor 25 is desirably vented to the atmosphere via line 29 at the top thereof and the aqueous starch suspension moves downwardly within reactor 25 which is operated almost liquid full and which is provided with a plurality of open compartments, compartments 25a, 25b, 25c, 25d and 25e. Within second stage atmospheric reactor 25 the aqueous starch suspension therein is maintained at a temperature of about 93°–100° C., such as 96° C., and flows downwardly therein in serial flow from an upper compartment to the next lower compartment. As illustrated, each of the compartments of reactor 25 is provided with mixing or agitating means 30a, 30b, 30c, 30d, 30e, respectively. Second stage atmospheric reactor 25 and the open compartments therein are adapted such that serial flow of the aqueous starch suspension from the upper compartment to the next lower compartment occurs with substantially no backflow of the aqueous starch suspension from a lower compartment to the next upper compartment.

The residence time of the aqueous starch suspension within atmospheric reactor 25 is in the range about 60–120 minutes, such as about 90 minutes, more or less, depending upon the temperature employed and the D.E. value desired in the thinned starch product. There issues from the bottom of second stage atmospheric reactor 25 via line 31 the desired thinned starch product, such as an aqueous thinned starch product having a D.E. value in the range 10–15.

If desired, second stage atmospheric reactor 25 may be operated isothermally or with a temperature gradient by providing cooling means or jackets, not illustrated, on the outside of reactor 25 for indirect cooling of the aqueous starch suspension undergoing treatment in accordance with this invention. Depending upon the temperature of the fluid being passed through the cooling means the temperature of the aqueous starch suspension within reactor 25 can be controlled. Like first stage reactor 12, second stage reactor 25 is provided with a substantial number of open compartments, such as about 10 in number, more or less, for serial flow of the aqueous starch suspension undergoing treatment therethrough.

In the operation of second stage atmospheric reactor 25 a uniform temperature, such as about 90°–100° C., may be employed or a temperature gradient may be employed, such as from a high temperature, about 96°–100° C., at the upper feed end of reactor 25 to a lower temperature of about 90°–92° C. at the lower product recovery end. In the practice of this invention it is preferred to use a temperature stable α-amylase, such as Thermamyl α-amylase supplied by Novo U.S. Corporation. In actual practice, however, it would appear that operating second stage reactor 25 at a relatively low temperature or with a temperature gradient would offer no advantage since the preferred α-amylase, Thermamyl α-amylase, is not inactivated rapidly at temperatures of about 93°–96° C. and, in fact, would be less active at lower temperatures. With a less temperature stable or temperature resistant α-amylase, there may be an advantage in employing a temperature gradient within second stage atmospheric reactor 25 or introducing the α-amylase thereinto at multiple points.

As will be apparent to those skilled in the art in the light of the foregoing disclosure, many modifications, alternations and substitutions are possible in the practice of this invention without departing from the spirit or scope thereof.

I claim:

1. A multi-stage process for the enzymatic thinning of starch employing the enzyme α-amylase which comprises forming an aqueous starch suspension, subjecting said aqueous starch suspension to a first stage thinning operation in the presence of added α-amylase, said first stage thinning operation being carried out at an initial temperature in the range 100°–110° C. for at least 3 minutes, and further heating the suspension at a final higher temperature of at least about 140° C. for at least about 3 minutes, said first stage thinning operation being carried out at a pressure sufficient to maintain the aqueous starch suspension being thinned in the liquid phase, thereupon subjecting the resulting enzymatically thinned starch suspension to atmospheric flashing to reduce the pressure of said resulting enzymatically thinned starch suspension to atmospheric pressure and to effect cooling thereof and subjecting the resulting treated starch suspension to a second stage thinning operation carried out at atmospheric pressure and at a temperature in the range 90°–100° C. in the presence of additional added α-amylase for at least 30 minutes to produce an aqueous thinned starch product.

2. A process in accordance with claim 1 wherein said aqueous starch suspension contains about 27–37% by weight starch.

3. A process in accordance with claim 1 wherein said aqueous starch suspension in said first stage thinning operation is held at said initial temperature of about 100°–110° C. for about 5–10 minutes.

4. A process in accordance with claim 1 wherein said aqueous thinned starch product has a D.E. value in the range about 10–20.

5. A process in accordance with claim 1 wherein said final temperature of said first stage thinning operation is in the range from about 140° C. to about 170° C.

6. A process in accordance with claim 1 wherein said aqueous starch suspension in said first stage thinning operation is held at said final temperature for a period of time in the range 3–8 minutes.

7. A process in accordance with claim 1 wherein said aqueous starch suspension to be thinned has a pH in the range from about 6.0 to about 7.0.

8. A process in accordance with claim 1 wherein said aqueous starch suspension to be thinned has a pH in the range of about 6.5.

9. A process in accordance with claim 1 wherein said aqueous starch suspension to be thinned has a dissolved calcium content of at least about 3–5 ppm by weight.

10. A process in accordance with claim 1 wherein the amount of added α-amylase present in said aqueous starch suspension to be thinned in said first stage thinning operation is in the range from about 0.03% to about 0.10% by weight based on the starch content of said aqueous starch suspension.

11. A process in accordance with claim 1 wherein said additional added α-amylase is added to said aqueous starch suspension undergoing treatment in said second stage in an amount in the range from about 0.1 to about 0.2% by weight based on the starch content of said aqueous starch suspension.

12. A process in accordance with claim 1 wherein the resulting treated starch suspension is held in said second stage thinning operation for a period of time in the range from about 60 minutes to about 120 minutes.

13. A process in accordance with claim 1 wherein the aqueous starch suspension leaving said first stage thinning operation is cooled atmospheric flashing to at least 100° C. before being introduced into said second stage thinning operation.

14. A process in accordance with claim 1 wherein said aqueous starch suspension is an aqueous suspension of corn starch.

15. A process in accordance with claim 1 wherein the pressure operative within said first stage is in the range from about 60 in about 200 psig.

* * * * *